(12) United States Patent
Villegas et al.

(10) Patent No.: US 10,517,917 B2
(45) Date of Patent: Dec. 31, 2019

(54) COMPOSITIONS AND METHODS FOR PREVENTING OR TREATING PULMONARY HYPERTENSION

(71) Applicant: THE REGENTS OF THE UNIVERSITY OF COLORADO, A BODY CORPORATE, Denver, CO (US)

(72) Inventors: Leah R. Villegas, Denver, CO (US); Myphuong T. Le, Denver, CO (US)

(73) Assignee: The Regents of the University of Colorado, a body corporate, Denver, CO (US)

(*) Notice: Subject to any disclaimer, the term of this patent is extended or adjusted under 35 U.S.C. 154(b) by 256 days.

(21) Appl. No.: 15/643,297

(22) Filed: Jul. 6, 2017

(65) Prior Publication Data
US 2018/0008662 A1    Jan. 11, 2018

Related U.S. Application Data

(60) Provisional application No. 62/360,075, filed on Jul. 8, 2016.

(51) Int. Cl.
| | | |
|---|---|---|
| A61K 36/00 | (2006.01) |
| A61K 38/01 | (2006.01) |
| A61K 9/00 | (2006.01) |
| A61K 36/738 | (2006.01) |
| A61K 36/52 | (2006.01) |
| A61K 36/61 | (2006.01) |
| A61K 36/07 | (2006.01) |
| A61K 36/82 | (2006.01) |
| A61K 36/185 | (2006.01) |
| A61K 36/634 | (2006.01) |
| A61K 36/539 | (2006.01) |
| A61K 36/85 | (2006.01) |
| A61K 36/38 | (2006.01) |
| A61P 11/00 | (2006.01) |
| A61P 9/12 | (2006.01) |
| A61K 47/10 | (2017.01) |

(Continued)

(52) U.S. Cl.
CPC .......... *A61K 38/011* (2013.01); *A61K 9/0019* (2013.01); *A61K 36/07* (2013.01); *A61K 36/185* (2013.01); *A61K 36/38* (2013.01); *A61K 36/52* (2013.01); *A61K 36/539* (2013.01); *A61K 36/61* (2013.01); *A61K 36/634* (2013.01); *A61K 36/738* (2013.01); *A61K 36/82* (2013.01); *A61K 36/85* (2013.01); *A61K 38/01* (2013.01); *A61K 47/10* (2013.01); *A61K 47/20* (2013.01); *A61P 9/12* (2018.01); *A61P 11/00* (2018.01); *A61K 45/06* (2013.01); *A61K 2236/13* (2013.01); *A61K 2236/15* (2013.01); *A61K 2236/333* (2013.01); *A61K 2236/53* (2013.01)

(58) Field of Classification Search
CPC ...................................................... A61K 36/00
See application file for complete search history.

(56) References Cited

PUBLICATIONS

Kao Corp., JP 2000-302633 A, Google Patents translation, 2000.*

* cited by examiner

*Primary Examiner* — Rosanne Kosson
(74) *Attorney, Agent, or Firm* — Saul Ewing Arnstein & Lehr LLP; Kathryn Doyle; Domingos J. Silva (57) ABSTRACT

The present invention provides a method of treating and/or preventing pulmonary hypertension in a subject in need thereof, the method comprising administering to the subject a therapeutically effective amount of a bioactive peptide preparation derived from at least one botanical source.

16 Claims, 5 Drawing Sheets

(51) Int. Cl.
*A61K 47/20* (2006.01)
*A61K 45/06* (2006.01)

FIG. 1A

Milling/pulvarization:
Increase surface area

Total protein extraction:
TCA/acetone wash
Phenol/SDS extraction
Methanol/ammonium acetate precipitation
Residual solvent evaporation

Peptide production:
Protein hydrolysis with Subtilisin A
Suspension in physiological buffer

COMPOSITIONS AND METHODS FOR PREVENTING OR TREATING PULMONARY HYPERTENSION

CROSS-REFERENCE TO RELATED APPLICATIONS

This application claims priority under 35 U.S.C. § 119(e) to U.S. Provisional Application No. 62/360,075, filed Jul. 8, 2016, which is incorporated herein by reference in its entirety.

BACKGROUND OF THE INVENTION

Pulmonary hypertension (PH) is a multifaceted disease characterized by high blood pressure in the lungs, a life-threatening complication with no cure but with ongoing research to develop better treatments. An important pathophysiological mechanism in PH is oxidative stress, which promotes abnormal vascular responses. Reactive oxygen species (ROS), such as superoxide ($O_2^-$), are potent activators of a variety of disease pathways. In blood vessels, changes in $O_2^-$ levels impact vascular tone, inflammation, cell growth and apoptosis. Elevated ROS in hypoxic pulmonary arteries can contribute to the development of PH. Superoxide dismutases (SODs) are the major natural antioxidant defense systems against $O_2^-$, operating by catalyzing the dismutation of $O_2^-$ into hydrogen peroxide ($H_2O_2$) and molecular oxygen ($O_2$).

Strategies for treating PH using compounds such as SOD mimetics are of great interest. For example, metalloporphyrins, a class of catalytic antioxidants, can scavenge a wide range of ROS. SOD mimetics are potent metal ion chelators that mimic the dismutation of $O_2^-$ and effectively block oxidative stress in vivo, including acute lung injury. However, SOD/catalase enzymes known in the art have only moderate efficacy due to two major limitations. First, pharmacokinetic studies of metalloporphyrins show that they are distributed only at moderate levels to the lungs and heart. Second, metalloporphyrins have short half-lives in living tissue.

Therefore, there remains a need in the art for methods and compounds for the treatment of pulmonary hypertension. In certain embodiments, these methods and compounds can prevent oxidative stress by scavenging free radicals and/or inhibiting the production of free radicals, such as reactive oxygen species. The present invention addresses this need.

BRIEF SUMMARY OF THE INVENTION

In one aspect, the invention provides a method of treating or preventing pulmonary hypertension in a subject. In certain embodiments, the method comprises administering to the subject in need thereof a therapeutically effective amount of a bioactive peptide preparation comprising an extract from at least one plant species selected from the group consisting of *Rosa damascena, Juglans nigra, Syzygium aromaticum, Inonotus obliquus, Camellia sinensis, Hypericum perforatum, Forsythia suspensa, Scutellaria lateriflora*, and *Verbena hastata*.

In certain embodiments, the bioactive peptide preparation inhibits or scavenges reactive oxygen species in the subject.

In certain embodiments, the preparation treats or alleviates one or more pulmonary hypertension symptoms selected from the group consisting of shortness of breath, fatigue, chest pressure, chest pain, abdominal pain, racing pulse, heart palpitations, poor appetite, nausea, lightheadedness, fainting, dizziness, swelling, cyanosis, abnormal blood pressure, and chronic cough.

In certain embodiments, the preparation comprises an extract that is insoluble in one or more solvents selected from the group consisting of trichloroacetic acid, acetone, methanol, an ammonium acetate solution (such as but not limited to a methanol solution thereof or methanol/water solution thereof), and any combinations thereof. In other embodiments, the preparation comprises a plant species extract that is soluble in phenol and/or sodium dodecyl sulfate (SDS).

In certain embodiments, the preparation comprises a plant extract produced through a process comprising washing a pulverized sample of the at least one plant species with trichloroacetic acid and/or acetone, thus generating a precipitate. In other embodiments, the precipitate is contacted with phenol and/or sodium dodecyl sulfate (SDS), thus generating a supernatant. In yet other embodiments, bioactive proteins are isolated from the supernatant.

In other embodiments, the process further comprises hydrolyzing the bioactive proteins in order to generate bioactive peptides.

In certain embodiments, the preparation is administered to the subject by at least one route selected from the group consisting of oral, nasal, inhalational, topical, buccal, rectal, pleural, peritoneal, intra-peritoneal, vaginal, intramuscular, subcutaneous, transdermal, epidural, intratracheal, otic, intraocular, intrathecal, and intravenous routes. In other embodiments, the preparation is administered to the subject through direct injection into the pulmonary artery.

In certain embodiments, the preparation is formulated as part of a pharmaceutical composition comprising one or more pharmaceutically acceptable carriers. In other embodiments, the method further comprises administering to the subject at least one additional compound useful for treating pulmonary hypertension. In yet other embodiments, the at least one additional compound is selected from the group consisting of vasodilators, vasoactive compounds, endothelin receptor antagonists, calcium channel blockers, guanylate cyclase stimulators, anticoagulants, anti-inflammatory agents and diuretics. In yet other embodiments, the at least one additional compound is selected from the group consisting of epoprostenol, iloprost, teprostinil, bosentan, macitentan, ambrisentan, sildenafil, tadalafil, diltiazem, nifedipine, adempas, warfarin, digoxin, metformin, or salts, solvates, enantiomers, diastereoisomers, and tautomers thereof. In yet other embodiments, the bioactive peptide preparation is co-formulated with the at least one additional compound.

In certain embodiments, the subject is a mammal. In other embodiments, the mammal is a human.

The invention further provides a pharmaceutical composition for treating pulmonary hypertension comprising an extract from at least one plant species selected from the group consisting of *Rosa damascena, Juglans nigra, Syzygium aromaticum, Inonotus obliquus, Camellia sinensis, Hypericum perforatum, Forsythia suspensa, Scutellaria lateriflora*, and *Verbena hastate*, wherein the extract is insoluble in trichloroacetic acid and/or acetone, and wherein the extract is soluble in phenol and/or sodium dodecyl sulfate (SDS).

In certain embodiments, the composition further comprises one or more pharmaceutically acceptable carriers. In other embodiments, the composition further comprises a therapeutically effective amount of at least one additional compound useful for treating pulmonary hypertension. In yet other embodiments, the at least one compound useful for treating PH is selected from the group consisting of vasodilators, vasoactive compounds, endothelin receptor antagonists, calcium channel blockers, guanylate cyclase stimulators, anticoagulants, anti-inflammatory agents and diuretics. In yet other embodiments, the at least one additional compound useful for treating PH is selected from the group consisting of epoprostenol, iloprost, teprostinil, bosentan, macitentan, ambrisentan, sildenafil, tadalafil, diltiazem, nifedipine, adempas, warfarin, digoxin, metformin, and salts, solvates, enantiomers, diastereoisomers, and tautomers thereof.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIGS. 2A-2B are histograms illustrating the frequencies of protein/peptide extracts with antioxidant activity from a botanical library.

FIGS. 4A-4B are bar graphs showing an analysis of pulmonary artery muscularization in hypoxic mice treated with BOT0073, BOT0322, a SOD mimetic (Mim) positive control or PBS negative control.

DETAILED DESCRIPTION OF THE INVENTION

The present invention relates to the unexpected discovery that bioactive peptide preparations comprising extracts from certain plants can be used to treat pulmonary hypertension in a subject in need thereof. Without intending to be limited to any one theory, the bioactive peptide preparations treat pulmonary hypertension by scavenging free radicals and/or inhibiting the production of free radicals, such as reactive oxygen species.

In certain embodiments, the bioactive peptide preparation comprises extracts from at least one plant species selected from the group consisting of *Rosa damascena, Juglans nigra, Syzygium aromaticum, Inonotus obliquus, Camellia sinensis, Hypericum perforatum, Forsythia suspensa, Scutellaria lateriflora* and *Verbena hastata*.

Definitions

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or within 10%, 9%, 8%, 7%, 6%, 5%, 4%, 3%, 2%, 1%, 0.5%, 0.1%, 0.05%, or 0.01% of the specified value, as such variations are appropriate to perform the disclosed methods. Unless otherwise clear from context, all numerical values provided herein are modified by the term about.

In one aspect, the terms "co-administered" and "co-administration" as relating to a subject refer to administering to the subject a compound and/or composition of the invention along with a compound and/or composition that may also treat or prevent a disease or disorder contemplated herein. In certain embodiments, the co-administered compounds and/or compositions are administered separately, or in any kind of combination as part of a single therapeutic approach. The co-administered compound and/or composition may be formulated in any kind of combinations as mixtures of solids and liquids under a variety of solid, gel, and liquid formulations, and as a solution.

By "effective amount" is meant the amount required to reduce or improve at least one symptom of a disease relative to an untreated patient. The effective amount of an active compound(s) used for therapeutic treatment of a disease varies depending upon the manner of administration, the age, body weight, and general health of the subject.

As used herein, the term "extract" refers to a concentrated preparation or solution of a compound or drug derived from a naturally occurring source, such as an herb or other plant material. Extracts may be prepared by a number of processes, including steeping an herb in solution, or drying and grinding an herb into a powder and dissolving the powder in a solution. An extract may be further concentrated by removing a portion of the solvent after dissolving an amount of the desired compound in the solution. An extract may also be strained or centrifuged to remove any solid material from the solution.

By "fragment" is meant a portion of a polynucleotide or nucleic acid molecule. This portion contains, preferably, at least 10%, 20%, 30%, 40%, 50%, 60%, 70%, 80%, or 90% of the entire length of the reference nucleic acids. A fragment may contain 10, 20, 30, 40, 50, 60, 70, 80, 90, or 100, 200, 300, 400, 500, 600, 700, 800, 900, 1000, 1500, 2000 or 2500 (and any integer value in between) nucleotides. The fragment, as applied to a nucleic acid molecule, refers to a subsequence of a larger nucleic acid. A "fragment" of a nucleic acid molecule may be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

As used herein, the term "functional fragment" refers to a truncated peptide or polypeptide of the parent that retains at least one biological, physiological, and/or pharmacological property of the parent.

The phrase "inhibit," as used herein, means to reduce a molecule, a reaction, an interaction, a gene and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein or a gene's stability, expression, function and activity, e.g., antagonists.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutical composition" or "pharmaceutically acceptable composition" refers to a mixture of at least one compound or molecule useful within the invention with a pharmaceutically acceptable carrier. The pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The terms "polypeptide" or "protein" or "peptide" as used herein refer to polymers in which the monomers are amino acid residues which are joined together through amide bonds. When the amino acids are alpha-amino acids, either the L-optical isomer or the D-optical isomer can be used, the L-isomers being preferred. The terms "polypeptide" or "protein" or "peptide" as used herein are intended to encompass any amino acid sequence and include modified sequences such as glycoproteins. The term "polypeptide" or "protein" or "peptide" is specifically intended to cover naturally occurring proteins, as well as those which are recombinantly or synthetically produced. It should be noted that the term "polypeptide" or "protein" includes naturally occurring modified forms of the proteins, such as glycosylated forms. The term "peptide" generally denotes a molecule comprising between 2 and about 50 amino acids.

As used herein, the terms "prevent," "preventing," "prevention," and the like refer to reducing the probability of developing a disorder or condition in a subject, who does not have, but is at risk of or susceptible to developing a disorder or condition.

As used herein, the term "subject," "patient" or "individual" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

As used herein, the term "therapeutically effective amount" is an amount of a compound of the invention, that when administered to a patient, treats, minimizes and/or ameliorates a symptom of the disease or disorder. The amount of a compound of the invention that constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

As used herein, the term "treatment" or "treating" is defined as the application or administration of a therapeutic agent, i.e., a compound useful within the invention (alone or in combination with another pharmaceutical agent), to a subject, or application or administration of a therapeutic agent to an isolated tissue or cell line from a subject (e.g., for diagnosis or ex vivo applications), who has pulmonary hypertension, a symptom of pulmonary hypertension or the potential to develop pulmonary hypertension, with the purpose to cure, heal, alleviate, relieve, alter, remedy, ameliorate, improve or affect pulmonary hypertension, the symptoms of pulmonary hypertension or the potential to develop pulmonary hypertension. Such treatments may be specifically tailored or modified, based on knowledge obtained from the field of pharmacogenomics.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

The following abbreviations are used herein: LV, left ventricle; PBS, phosphate buffered saline; PH, pulmonary hypertension; ROS, reactive oxygen species; RV, right ventricle; RVSP, right ventricular systolic pressure; RV/LV+S, right ventricular/left ventricular+septum; SDS-PAGE, sodium dodecyl sulfate poly-acrylamide gel electrophoresis; SOD, superoxide dismutase; TAC, total anti-oxidant capacity.

Compositions

The invention further provides a pharmaceutical composition for treating pulmonary hypertension comprising an extract from at least one plant species selected from the group consisting of *Rosa damascena, Juglans nigra, Syzygium aromaticum, Inonotus obliquus, Camellia sinensis, Hypericum perforatum, Forsythia suspensa, Scutellaria lateriflora*, and *Verbena hastate*. In certain embodiments, the extract is insoluble in trichloroacetic acid and/or acetone. In other embodiments, the extract is soluble in phenol and/or SDS.

In certain embodiments, the composition further comprises one or more pharmaceutically acceptable carriers. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-peritoneal, intra-arterial, intravenous, intrabronchial, inhalation, and topical administration.

In certain embodiments, the composition further comprises a therapeutically effective amount of at least one additional compound useful for treating pulmonary hypertension. In other embodiments, the at least one compound useful for treating PH is selected from the group consisting of vasodilators, vasoactive compounds, endothelin receptor antagonists, calcium channel blockers, guanylate cyclase stimulators, anticoagulants, anti-inflammatory agents and diuretics. In yet other embodiments embodiments, the at least one additional compound useful for treating PH is selected from the group consisting of epoprostenol, iloprost, teprostinil, bosentan, macitentan, ambrisentan, sildenafil, tadalafil, diltiazem, nifedipine, adempas, warfarin, digoxin, metformin, and salts, solvates, enantiomers, diastereoisomers, and tautomers thereof.

Methods

The present invention provides a method of treating and/or preventing pulmonary hypertension in a subject in need thereof. In certain embodiments, the method comprises administering to the subject a therapeutically effective amount of a bioactive peptide preparation.

In certain embodiments, the preparation comprises extracts from at least one plant species selected from the group consisting of *Rosa damascena, Juglans nigra, Syzygium aromaticum, Inonotus obliquus, Camellia sinensis, Hypericum perforatum, Forsythia suspensa, Scutellaria lateriflora* and *Verbena hastata*.

In other embodiments, the preparation has antioxidant capacity. In yet other embodiments, the preparation has free radical and/or reactive oxygen species (ROS) inhibitory and/or scavenging activity.

In yet other embodiments, the preparation has at least one effect selected from the group consisting of: increased small muscularized vessels (<50 μm), decreased pulmonary artery medial wall thickness, reduction in right ventricular systolic pressure and reduction in right ventricular hypertrophy.

In certain embodiments, the preparation treats or alleviates one or more symptoms associated with pulmonary hypertension selected from the group consisting of shortness of breath, fatigue, chest pressure, chest pain, abdominal pain, racing pulse, heart palpitations, poor appetite, nausea, lightheadedness, fainting, dizziness, swelling, cyanosis, abnormal blood pressure and chronic cough.

In certain embodiments, the preparation comprises an extract that is insoluble in one or more solvents selected from trichloroacetic acid, acetone, methanol, an ammonium acetate solution, and any combinations thereof. In other embodiments, the preparation comprises an extract that is soluble in phenol and/or sodium dodecyl sulfate.

In certain embodiments, the method of producing the extract comprises pulverizing a botanical sample. In other embodiments, the sample is washed in one or more solutions of trichloroacetic acid and/or acetone, thus generating a precipitate. In yet other embodiments, the precipitate is collected and mixed with a solution comprising phenol and/or sodium dodecyl sulfate to form a mixture. In yet other embodiments, the mixture is vortexed. In yet other embodiments, the mixture is centrifuged. In yet other embodiments, the phenol solution supernatant is collected. In yet other embodiments, bioactive proteins are precipitated from the phenol solution supernatant. In yet other embodiments, the bioactive proteins are further subjected to hydrolysis to generate bioactive peptides.

In certain embodiments, the preparation is administered to the subject by at least one route selected from the group consisting of oral, nasal, inhalational, topical, buccal, rectal, pleural, peritoneal, intra-peritoneal, vaginal, intramuscular, subcutaneous, transdermal, epidural, intratracheal, otic, intraocular, intrathecal, and intravenous routes.

In certain embodiments, a targeted delivery of the antioxidant increases its therapeutic levels and enhances its protective effects at the site of injury. In certain embodiments, the site of injury is the lung and/or pulmonary artery.

In certain embodiments, the preparation is administered directly to the lungs and/or pulmonary artery through an injection. In other embodiments, the preparation is administered directly to the lungs and/or pulmonary artery through inhalation of an aerosolized composition comprising the bioactive peptide preparation.

In certain embodiments, the bioactive peptide preparation is formulated as part of a pharmaceutical composition comprising one or more pharmaceutically acceptable carriers.

In certain embodiments, the method of the invention further comprise administration of at least one additional compound (or composition) useful for treating PH. In certain embodiments, the bioactive peptide preparation is administered concurrently with the at least one additional compound. In other embodiments, the bioactive peptide preparation is administered to the subject before the at least one additional compound. In yet other embodiments, the bioactive peptide preparation is administered to the subject after the at least one additional compound. In other embodiments, the bioactive peptide preparation is co-formulated with the at least one additional compound.

In certain embodiments, the therapeutically effective amount of the composition ranges from about 0.001 mg/day to about 1,000 mg/day.

In certain embodiments, the bioactive peptide preparation is administered to the subject orally. In other embodiments, the one or more bioactive peptide preparation is administered in one or more forms selected from the group consisting of a pill, tablet, capsule, soup, tea, concentrate, dragees, liquids, drops, and gelcaps.

In certain embodiments, the subject is a mammal. In other embodiments, the subject is human.

Combination Therapies

In certain embodiments, the extracts of the invention are useful in the methods of present invention when used concurrently with at least one additional compound useful for treating PH.

In a non-limiting example, the compounds of the invention may be used concurrently or in combination with a therapeutically effective amount of at least one compound selected from the group consisting of vasodilators, vasoactive compounds, endothelin receptor antagonists, calcium channel blockers, guanylate cyclase stimulators, anticoagulants, anti-inflammatory agents and diuretics. In certain embodiments, the at least one additional compound useful for treating PH is selected from the group consisting of epoprostenol, iloprost, teprostinil, bosentan, macitentan, ambrisentan, sildenafil, tadalafil, diltiazem, nifedipine, adempas, warfarin, digoxin, metformin, and salts, solvates, enantiomers, diastereoisomers, and tautomers thereof.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to elsewhere herein may be applied to experimental data to generate a corresponding graph to aid in assessing the effects of the drug combination. The corresponding graphs associated with the equations referred to elsewhere herein are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 1,000 mg/kg of body weight/per day. The pharmaceutical compositions useful for practicing the invention may be administered to deliver a dose of from 1 ng/kg/day and 100 mg/kg/day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated in the invention.

In certain embodiments, the compositions of the invention are formulated using one or more pharmaceutically acceptable excipients or carriers. In other embodiments, the pharmaceutical compositions of the invention comprise a therapeutically effective amount of a compound of the invention and a pharmaceutically acceptable carrier. In yet other embodiments, the compound of the invention is the only biologically active agent (i.e., capable of treating pulmonary hypertension) in the composition. In yet other embodiments, the compound of the invention is the only biologically active agent (i.e., capable of treating pulmonary hypertension) in therapeutically effective amounts in the composition.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds and/or compositions of the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 400 mg to about 6,000 mg, about 500 mg to about 5,000 mg, about 750 mg to about 4,000 mg, about 1,000 mg to about 3,000 mg, about 1,000 mg to about 2,500 mg, about 20 mg to about 2,000 mg and any and all whole or partial increments therebetween. In certain embodiments, the dose of the compounds and/or compositions of the invention is about 800 mg.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

Routes of administration of any of the compositions of the invention include oral, nasal, rectal, intravaginal, parenteral, buccal, sublingual, topical, or inhalational. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-peritoneal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are soups, teas, concentrates, tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation". For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of a disease or disorder contemplated in the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intra-peritoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Aerosolized Administration

Routes of administration of any of the compositions of the invention include nasal, inhalational, intratracheal, intrapulmonary, intrabronchial, and inhalation.

Suitable compositions and dosage forms include, for example, dispersions, suspensions, solutions, syrups, granules, beads, powders, pellets, liquid sprays for nasal or oral administration, dry powder or aerosolized formulations for inhalation, and the like. It should be understood that the formulations and compositions that would be useful in the present invention are not limited to the particular formulations and compositions that are described herein.

Powdered and granular formulations of a pharmaceutical preparation of the invention may be prepared using known methods. Such formulations may be administered directly to a subject, used, for example, to form a material that is suitable to administration to a subject. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may be prepared, packaged, or sold in a formulation suitable for pulmonary administration via the buccal cavity. Such a formulation may comprise dry particles that comprise the active ingredient and have a diameter in the range from about 0.5 to about 7 nanometers, and in certain embodiments from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In certain embodiments, such powders comprise particles wherein at least 98% of the particles by weight have a diameter greater than 0.5 nanometers and at least 95% of the particles by number have a diameter less than 7 nanometers. In certain embodiments, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in certain embodiments having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration in certain embodiments have an average diameter in the range from about 0.1 to about 200 nanometers. The pharmaceutical composition of the invention may be delivered using an inhalator such as those recited in U.S. Pat. No. 8,333,192 B2, which is incorporated herein by reference in its entirety.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds useful within the methods of the invention may be administered in the form of microparticles, for example by injection, or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any and all whole or partial increments thereof after drug administration.

Dosing

The therapeutically effective amount or dose of a compound of the present invention depends on the age and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 5 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 5 or more times per day). When multiple daily doses are used, the unit dosage form may be the same or different for each dose.

Toxicity and therapeutic efficacy of such therapeutic regimens are optionally determined in experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Materials and Methods
Total Protein Extraction and Hydrolysis

Botanical and fungal specimens were stored at −20° C. Specimens were subjected to total protein extraction using a phenol/SDS method (Rodrigues, et al., 2012, Genetics and molecular biology 35:348-352; Wang, et al., 2006, Electrophoresis 27:2782-278). Briefly, botanicals were first pulverized using a food mill, then washed in cold TCA/acetone (10% trichloroacetic acid (w/v) in acetone) (Sigma-Aldrich, St. Louis, Mo.), followed by two washes in cold acetone. The precipitates were then mixed in equal parts (v/v) Phenol (Tris-saturated, pH 8.0) (Sigma-Aldrich, St. Louis, Mo.) and SDS buffer (1% SDS (w/v), 30% sucrose (w/v), 100 mM Tris-HCl, pH 8.8) (Sigma-Aldrich, St. Louis, Mo.) and vortexed for two hours at room temperature to extract proteins. The phases were then separated by centrifugation at 3,000×g for 20 minutes at room temperature, and the top phenol phase (containing the proteins) were transferred to a new tube. The proteins were precipitated from the phenol phase using ammonium acetate solution (100 mM ammonium acetate in methanol) (Sigma-Aldrich, St. Louis, Mo.). The protein precipitates were then washed three times in ammonium acetate solution, followed by a final wash in acetone. The solvents were discarded and residual solvents were removed using a parallel solvent evaporation system (Buchi Laboratories, Flawil, Switzerland). The final protein products were resuspended in phosphate buffered saline (1×PBS, pH 7.4) (Mediatech, Inc., Tewksbury, Mass.) and stored at −80° C. Total proteins were then subjected to hydrolysis to generate peptides (Doucet, et al., 2003, Journal of agricultural and food chemistry 51:6300-6308). Briefly, 250-1000 ug of protein extract were incubated with 24.3 mU Subtilisin A (Sigma-Aldrich, St. Louis, Mo.) in PBS. The mixture was incubated at 50° C. for four hours then heat inactivated at 80° C. for 15 minutes.

SDS-PAGE

Figure 1A:
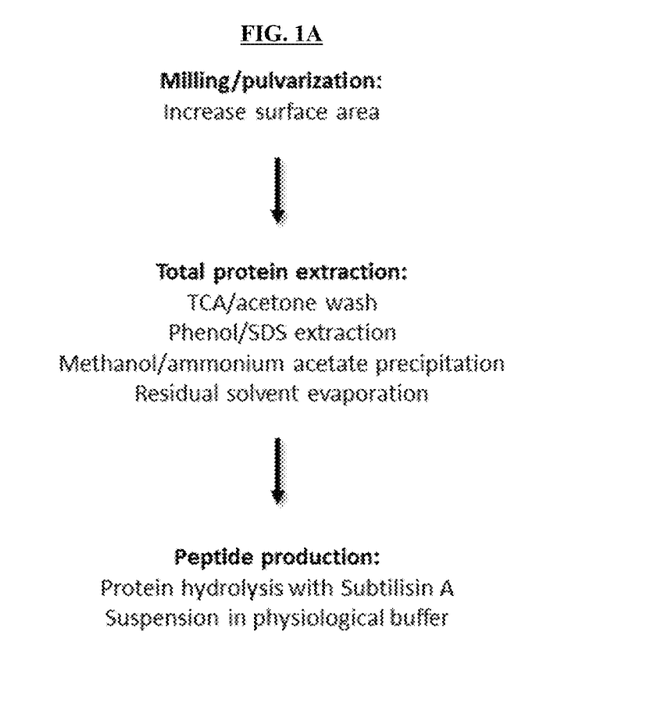
FIG. 1A is a diagram describing methods for total protein extraction and peptide production.
Figure 1B:
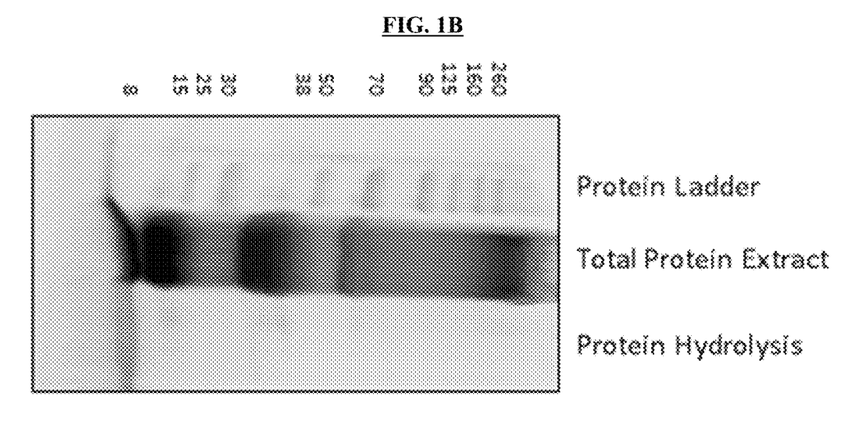
FIG. 1B is a representative illustration of total protein extract and protein hydrolysis with ALCALASE® enzyme.

Protein/peptide extracts were subjected to sodium dodecyl sulfate poly-acrylamide gel electrophoresis (SDS-PAGE) to quantify total protein content and verify hydrolysis. After gel electrophoresis, the proteins were stained with Odyssey IRDye Blue Protein Stain and imaged using the Odyssey Imaging System (Licor, Lincoln, Nebr.). FIG. 1 illustrates representative samples of total protein extracts and hydrolysis.

Antioxidant Assays

The protein/peptide extracts were screened using two antioxidant activity assays: Total Antioxidant Capacity (TAC) Assay (Cell Biolabs, Inc., San Diego, Calif.) and SOD Assay Kit-WST (Dojindo Molecular Technologies, Inc., Rockville, Md.) according to manufacturers' protocol. The potency ($ED_{50}$) of the top extract candidates was determined by dose-response titration of extracts. The top extract candidates were then subjected to a xanthine oxidase inhibitor assay (XO assay). Each extract was added to the reaction buffer (50 mM K2HPO4, pH 7.5; 0.1 mM EDTA, 15 mU/mL xanthine oxidase) then activated with 500 uM xanthine. The production of uric acid was measured kinetically at 305 nm 37° C. every minute for 60 minutes, in a BioTek (BioTek Instruments, Inc., Winooski, Vt.). Assay controls included reactions without peptide extracts (PBS only), with or without xanthine substrate. Positive inhibitor control reactions included allopurinol.

Hypoxic Mouse Model and Antioxidant Treatment

Studies were performed on 4 week old, C57/BL6 male mice (Jackson Lab, Bar Harbor, Me.) maintained in normobaric normoxia or hypobaric hypoxia for up to 21 days. The hypoxia exposures were performed in hypobaric chambers at a simulated altitude of 18,000 ft above sea level (395 torr), conditions equivalent to 10% atmospheric oxygen. Normobaric conditions were at approximately 5,000 ft above sea level (Denver, Colo.). Tail vein injections of phosphate buffered saline (PBS) or 5-7 mg/kg of peptide extract dissolved in PBS (100 uL total volume) were given 3 times for the first week, beginning on day 1 of hypoxic exposure or under normoxic conditions. Due to limitations of the tail vein injection technique and tail trauma, the mice were given fewer injections, 2 times on the second week and 1 time on the third week. Hemodynamic measurements and lung tissue were taken according to the protocols as described elsewhere herein.

Assessment of Pulmonary Hypertension

Mice were anesthetized by inhaled isofluorane (2-4%) mixed with room air (21% oxygen, 79% nitrogen). Right ventricular systolic pressure (RVSP) was measured by direct RV puncture in a closed chest. A 25-gauge needle attached to a pressure transducer was introduced into the RV and live pressure tracings were measured using the Cardiomax III Cardiac Output program (Columbus Instruments). Pressures were monitored for at least 30 seconds, and averaged every 10 seconds to account for beat to beat variability. The blood was then drained from the lungs and heart by flushing 5 mL cold PBS into the right ventricle. The hearts were resected, the right and left ventricle (including the septum) were separated under a dissecting microscope, then weighed. Right ventricular hypertrophy was quantified by comparing the ratio of the right ventricular/left ventricular+septum weights (RV/LV+S).

Lung Histology and Analysis of Pulmonary Artery Muscularization

Lungs were flushed through the pulmonary artery with PBS, then tissue was inflation fixed, embedded and sectioned for immunohistochemistry according to previous method. Briefly, the left lung was inflation fixed at 20 cm $H_2O$ pressure in 4% paraformaldehyde for 30 minutes and then dissected from the chest cavity and placed in 4% paraformaldehyde at 4° C. for two days. Lungs were then transferred to 70% ethanol, paraffin embedded, and sectioned. Lung sections were immunostained with mouse monoclonal α-smooth muscle actin antibody (1:100, Clone 1A4). The block, secondary antibody, and ABC reagent were provided in the Mouse-on-Mouse kit (Vector Laboratories) for the mouse monoclonal antibodies. The slides were developed with ImmPact DAB diluent (Vector Laboratories) and counterstained with hematoxylin. Tissue sections were examined by brightfield microscopy and imaged using the Aperio CS2 ScanScope (Leica Biosystems Inc., Buffalo Grove, Ill.). The images were analyzed using Aperio ImageScope 12.3. The number of small vessels with positive α-SMA staining was counted in 10 fields of view (10× magnification) to quantify the number of muscularized small pulmonary vessels (30-50 um). Morphometric analysis of pulmonary arteries was performed by defining the area of the medial wall, or α-SMA staining of vessels (100-200 um, 40× magnification). The analysis of α-SMA staining was evaluated by an investigator blinded to treatment groups.

Example 1: Identification of Candidate Bioactive Peptide Extracts

Figure 2A:
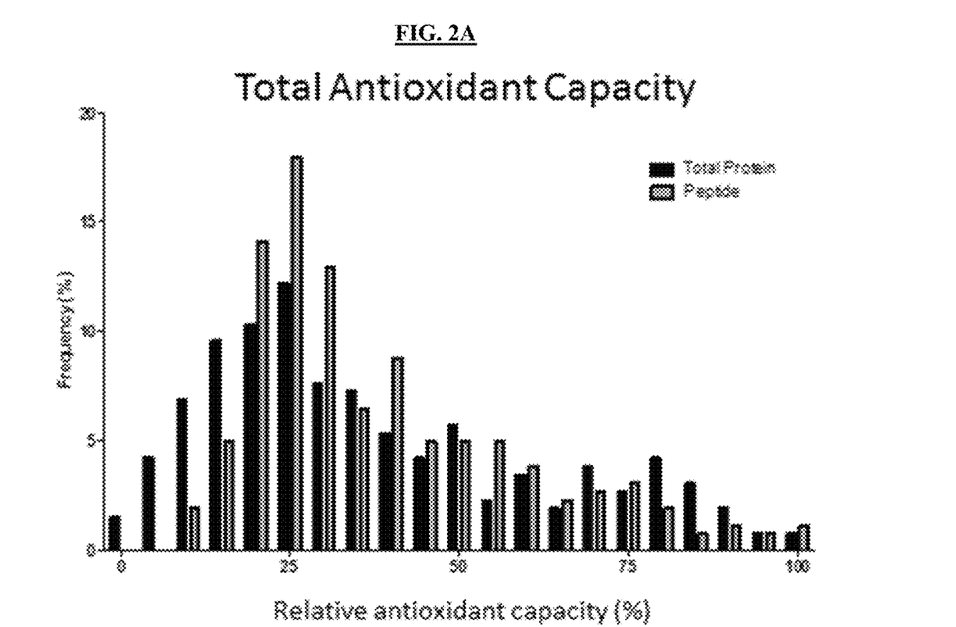
FIG. 2A reports the percentage of proteins and peptides with low (25%), medium (50%) and high (100%) total antioxidant capacity.
Figure 2B:
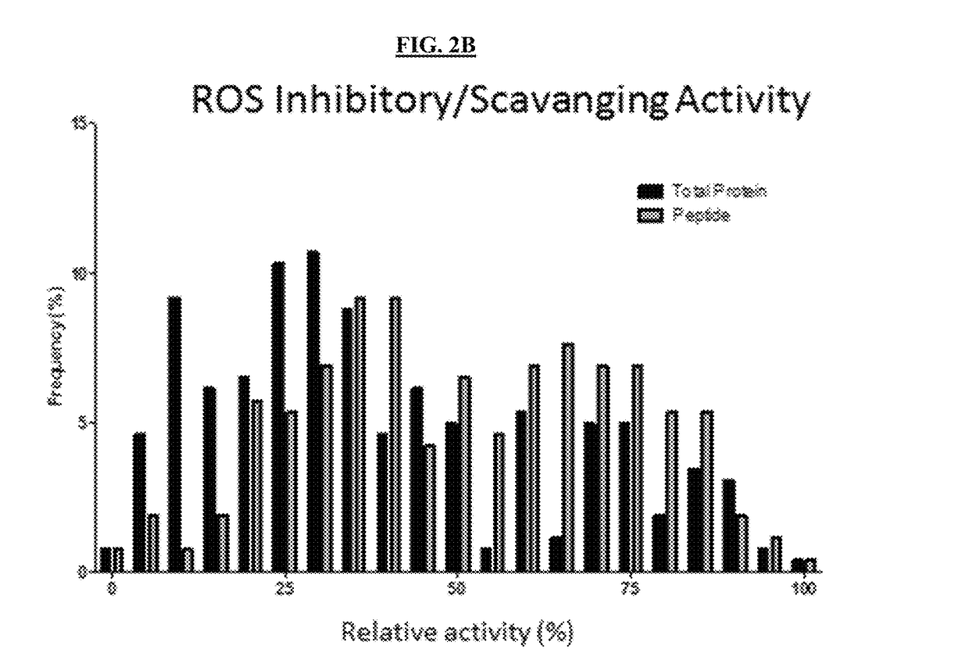
FIG. 2B reports the percentage of proteins and peptides based on relative ROS inhibitory/scavenging activity.

Methods were developed to extract total protein and generate a bioactive peptide library from 320 plant and fungal sources (FIGS. 1A-1B). FIGS. 2A-2B illustrate the frequencies of protein/peptide extracts with antioxidant activity from botanical library. The total antioxidant capacity (TAC) of each protein and peptide extract was measured based on the reduction of copper (II) to copper (I) (FIG. 2A). The ROS inhibitory/scavenging properties of each protein and peptide extract was measured based on the detection of superoxide anion produced from xanthine oxidase (FIG. 2B). While both protein and peptide extracts contained antioxidant activities, generally, hydrolysis of proteins (peptides) maintained or had higher activity than non-hydrolyzed proteins indicating the release of bioactive domains.

The peptide extracts having the highest relative TAC were subjected to dose-response titrations to determine the relative effective doses and potencies as indicated in Table 1. The botanical sources of the top five extracts were: pink roses (*Rosa Damascena*), black walnut hull (*Juglans nigra*), clove (*Syzgium aromaticum*), Chaga mushroom (*Inonotus obliquus*), Lapsang Souchong tea (*Camelia sinesis*).

The extracts having the highest relative ROS scavenging/inhibition activity were subjected to dose-response titrations to determine the relative effective doses and potencies as indicated in Table 2. The botanical sources of the top five extracts were: St. John's wort (*Hypericum perforatum*), forsythia fruit (*Forsythia suspensa*), Chaga mushroom (*Inonotus obliquus*), skullcap (*Scutellaria lateriflora*), blue vervain (*Verbena hastata*).

These top peptide extracts were then subjected to an XO assay to determine whether the peptides specifically had XO inhibitory activity. Two peptide extracts, black walnut hull (20.5% inhibition at 0.0125 ug/uL concentration) and clove (56.65% inhibition at 0.1 ug/uL concentration), showed specific XO inhibitory activity (Table 3). However, no XO inhibitory activity were detected in other peptide extracts, indicating that the antioxidant activity were most likely ROS scavenging activity.

Figure 3A:
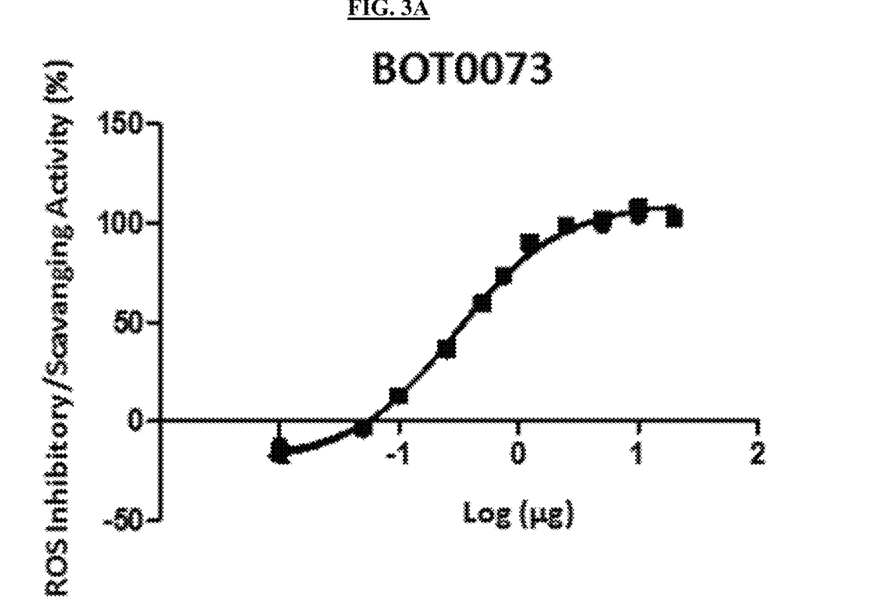
FIGS. 3A-3B are graphs showing the median effective doses of extract BOT0073 (FIG. 3A) and BOT0322 (FIG. 3B) for treating hypoxia-induced PH in mouse models.
Figure 3B:
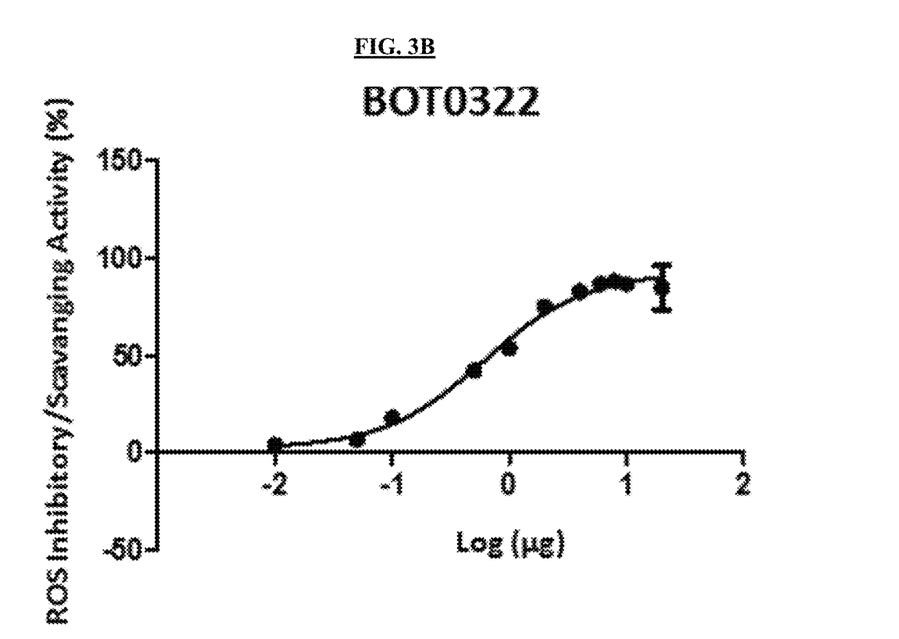

The peptide extracts with lowest $ED_{50}$ (ROS inhibition/scavenging assay) used in subsequent animal studies were BOT0073 (*Inonotus obliquus*, Chaga mushroom, $ED_{50}$=0.3024±0.0158 ug) and BOT0322 (*Scutellaria lateriflora*, skullcap, $ED_{50}$=0.6152±0.0856 ug), as illustrated in FIGS. 3A-3B.

TABLE 1

| Botanical ID# | Common Name | Genus/Species | Total Antioxidant Capacity (CRE, μM) | $ED_{50}$ (μg) |
|---|---|---|---|---|
| BOT0284 | Pink Roses | *Rosa damascene* | 2680.0 | 0.0506 ± 0.0017 |
| BOT0123 | Black Walnut Hull Powder | *Juglans nigra* | 1919.1 | 0.0765 ± 0.0147 |
| BOT0168 | Clove Powder | *Syzgium aromaticum* | 1808.1 | 1.118 ± 0.0021 |
| BOT0073 | Chaga Mushroom Powder | *Inonotus obliquus* | 1763.7 | 1.203 ± 0.0120 |
| BOT0007 | Lapsang Souchong Tea | *Camellia sinensis* | 1734.5 | 0.0308 ± 0.0003 |

TABLE 2

| Botanical ID# | Common Name | Genus/Species | ROS Inhibition/Scavenging (Activity, %) | $ED_{50}$ (μg) |
|---|---|---|---|---|
| BOT0330 | St. John's Wort | *Rosa damascene* | 118.4 | 4.204 ± 0.7077 |
| BOT0198 | Forsythia Fruit Powder | *Juglans nigra* | 98.9 | 0.9618 ± 0.0400 |
| BOT0073 | Chaga Mushroom Powder | *Inonotus obliquus* | 97.7 | 0.3024 ± 0.0158 |
| BOT0322 | Skullcap | *Scutellaria lateriflora* | 95.7 | 0.6152 ± 0.0856 |
| BOT0130 | Blue Vervain | *Verbena hastata* | 94.1 | 2.103 ± 0.0573 |

TABLE 3

| Botanical ID# | Common Name | Genus/Species | Detectable concentration (μg/μL) | XO inhibitory activity (%) |
|---|---|---|---|---|
| BOT0123 | Black Walnut Hull Powder | *Juglans nigra* | 0.0125 | 20.5 |
| BOT0168 | Clove Powder | *Syzgium aromaticum* | 0.1 | 56.6 |

Figure 4A:
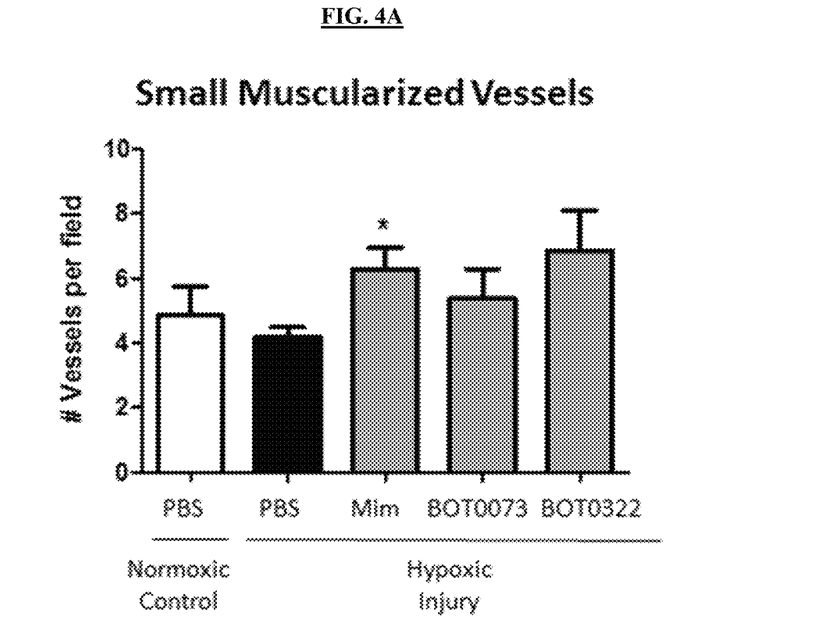
FIG. 4A reports the number of small, distal muscularized vessels, showing an increase in the hypoxic mice treated with antioxidants and FIG. 4B reports the attenuation of medial wall thickening. #=$p<0.05$ compared to NX control; *=$p<0.05$ compared to PBS control.
Figure 4B:
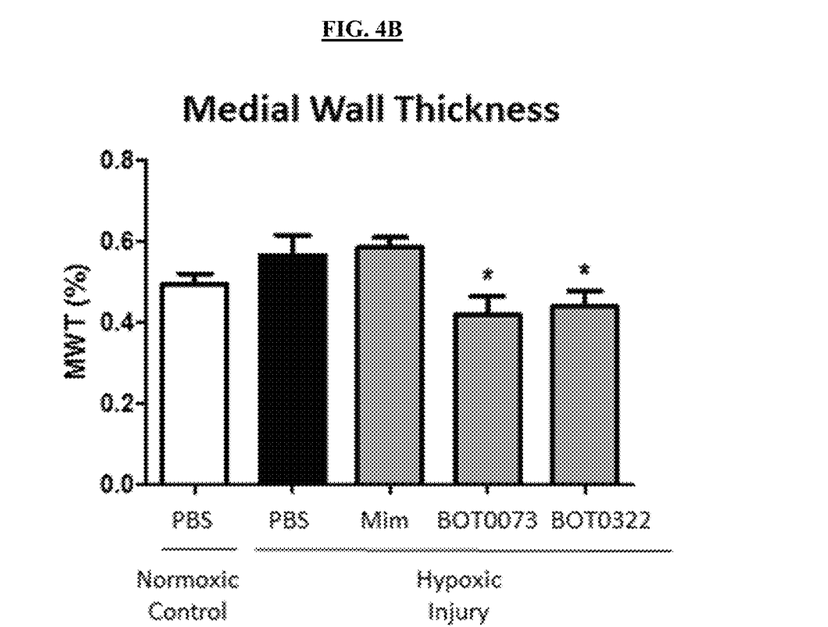

Example 2: Assessment of Protective Effects in Mouse Model of Hypoxia-induced PH In the analysis of pulmonary artery muscularization in hypoxic mice treated with BOT0073, BOT0322, a SOD mimetic (Mim) positive control, or PBS negative control there was increased number of small, distal muscularized vessels (FIG. 4A) and attenuation of medial wall thickening (FIG. 4B) in the hypoxic mice treated with antioxidants (#=p<0.05 compared to NX control; *=p<0.05 compared to PBS control). Pulmonary hypertension is characterized by loss of pulmonary microvasculature and medial wall thickening of all pulmonary arteries. Treatment with peptide extracts suggest restoration of the pulmonary microcirculation and prevention of vascular remodeling.

Figure 5A:
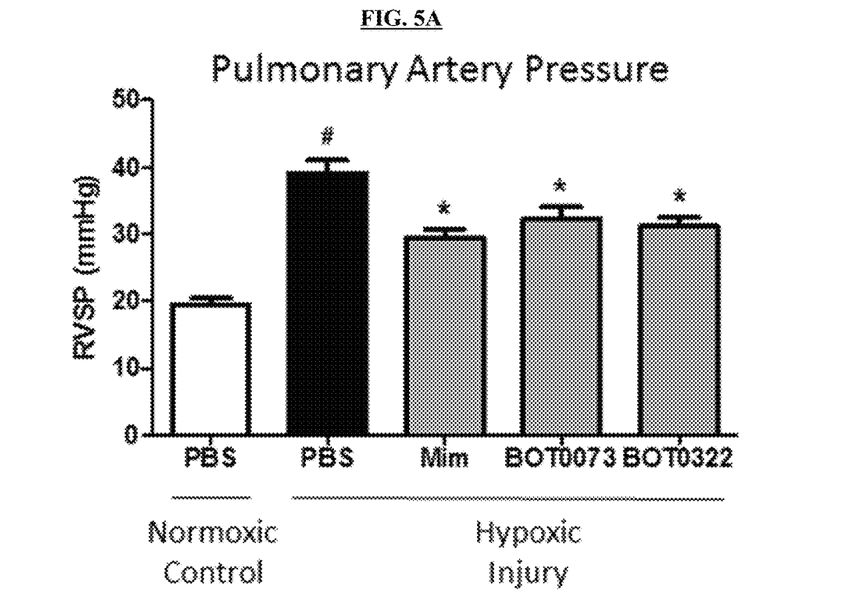
FIGS. 5A-5B are bar graphs showing an analysis of pulmonary hypertension in hypoxic mice treated with BOT0073, BOT0322, a SOD mimetic (Mim) positive control, or PBS negative control. Attenuation of right ventricular systolic pressure (FIG. 5A) and right ventricular hypertrophy (FIG. 5B) in hypoxic mice treated with antioxidants are reported. #=$p<0.05$ compared to NX control; *=$p<0.05$ compared to PBS control.
Figure 5B:
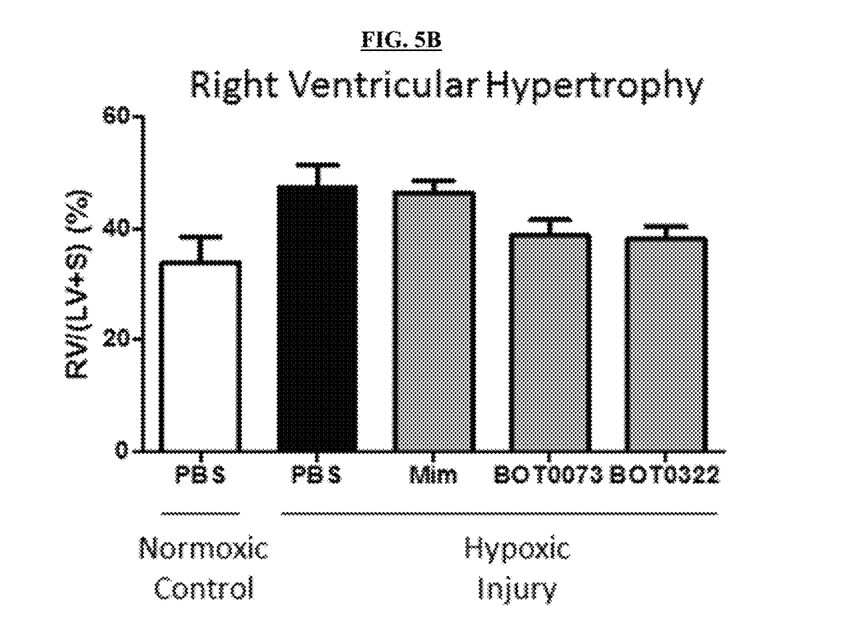

Example 3: Antioxidant Peptides Attenuate Hypoxia-induced Pulmonary Hypertension and Right Ventricular Hypertrophy In hypoxic mice treated with BOT0073, BOT0322, a SOD mimetic (Mim) positive control, or PBS negative control, there was attenuation of right ventricular systolic pressure (FIG. 5A) and right ventricular hypertrophy (FIG. 5B) in hypoxic mice treated with antioxidants (#=p<0.05 compared to NX control; *=p<0.05 compared to PBS control). Pulmonary hypertension is characterized by increased RVSP and RV hypertrophy. Attenuation of RVSP and RV hypertrophy suggest peptide extracts have protective and/or reversal effects against hypoxia-induced pulmonary hypertension.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating pulmonary hypertension in a subject, the method comprising administering to the subject in need thereof a therapeutically effective amount of a bioactive peptide preparation comprising an extract from at least one plant species selected from the group consisting of *Rosa damascena, Juglans nigra, Inonotus obliquus, Camellia sinensis, Hypericum perforatum, Forsythia suspensa, Scutellaria lateriflora,* and *Verbena hastata.*

2. The method of claim 1, wherein the preparation inhibits or scavenges reactive oxygen species in the subject.

3. The method of claim 1, wherein the preparation treats or alleviates one or more pulmonary hypertension symptoms selected from the group consisting of shortness of breath, fatigue, chest pressure, chest pain, abdominal pain, racing pulse, heart palpitations, poor appetite, nausea, lightheadedness, fainting, dizziness, swelling, cyanosis, abnormal blood pressure, and chronic cough.

4. The method of claim 1, wherein the preparation comprises a plant species extract that is insoluble in at least one solvent selected from the group consisting of trichloroacetic acid, acetone, methanol, an ammonium acetate solution, and any combinations thereof.

5. The method of claim 1, wherein the preparation comprises a plant species extract that is soluble in at least one selected from the group consisting of phenol and sodium dodecyl sulfate (SDS).

6. The method of claim 1, wherein the preparation comprises a plant extract produced through a process comprising:
   a) washing a pulverized sample of the at least one plant species with at least one solvent selected from the group consisting of trichloroacetic acid, acetone, methanol, and an ammonium acetate solution, thus generating a precipitate;
   b) contacting the precipitate with at least one solution selected from the group consisting of a solution of phenol and a solution of sodium dodecyl sulfate (SDS), thus generating a supernatant; and
   c) isolating bioactive proteins from the supernatant.

7. The method of claim 6, wherein the process further comprises hydrolyzing the bioactive proteins in order to generate bioactive peptides.

8. The method of claim 1, wherein the preparation is administered to the subject by at least one route selected from the group consisting of oral, nasal, inhalational, topical, buccal, rectal, pleural, peritoneal, intra-peritoneal, vaginal, intramuscular, subcutaneous, transdermal, epidural, intratracheal, otic, intraocular, intrathecal, and intravenous routes.

9. The method of claim 8, wherein the preparation is administered to the subject through direct injection into the pulmonary artery.

10. The method of claim 1, wherein the preparation is formulated as part of a pharmaceutical composition comprising one or more pharmaceutically acceptable carriers.

11. The method of claim 1, further comprising administering to the subject at least one additional compound useful for treating pulmonary hypertension.

12. The method of claim 11, wherein the at least one additional compound is selected from the group consisting of vasodilators, vasoactive compounds, endothelin receptor antagonists, calcium channel blockers, guanylate cyclase stimulators, anticoagulants, anti-inflammatory agents and diuretics.

13. The method of claim 11, wherein the at least one additional compound is selected from the group consisting of epoprostenol, iloprost, teprostinil, bosentan, macitentan, ambrisentan, sildenafil, tadalafil, diltiazem, nifedipine, adempas, warfarin, digoxin, metformin, or salts, solvates, enantiomers, diastereoisomers, and tautomers thereof.

14. The method of claim 11, wherein the bioactive peptide preparation is co-formulated with the at least one additional compound.

15. The method of claim 1, wherein the subject is a mammal.

16. The method of claim 15, wherein the mammal is a human.

* * * * *